US010705052B2

(12) United States Patent
Hattori

(10) Patent No.: US 10,705,052 B2
(45) Date of Patent: Jul. 7, 2020

(54) GAS SENSOR

(71) Applicant: TAIYO YUDEN CO., LTD., Chuo-ku, Tokyo (JP)

(72) Inventor: Masashi Hattori, Takasaki (JP)

(73) Assignee: TAIYO YUDEN CO., LTD., Tokyo (JP)

( * ) Notice: Subject to any disclaimer, the term of this patent is extended or adjusted under 35 U.S.C. 154(b) by 149 days.

(21) Appl. No.: 15/666,427

(22) Filed: Aug. 1, 2017

(65) Prior Publication Data

US 2018/0045682 A1 Feb. 15, 2018

(30) Foreign Application Priority Data

Aug. 9, 2016 (JP) .................................. 2016-156089

(51) Int. Cl.
*G01N 29/036* (2006.01)
*G01N 33/00* (2006.01)

(52) U.S. Cl.
CPC ....... *G01N 29/036* (2013.01); *G01N 33/0047* (2013.01); *G01N 2291/014* (2013.01);
(Continued)

(58) Field of Classification Search
CPC ......... G01N 2291/0426; G01N 29/022; G01N 29/2443; G01N 1/00; G01N 27/12;
(Continued)

(56) References Cited

U.S. PATENT DOCUMENTS 5,087,679 A * 2/1992 Inukai .................... H01B 3/443
361/317
5,411,709 A * 5/1995 Furuki ................. G01N 21/643
422/83

(Continued)

FOREIGN PATENT DOCUMENTS

CN 101871873 A 10/2010
CN 102209890 A 10/2011

(Continued)

OTHER PUBLICATIONS

Regmi, Bishnu Prasad, "GUMBOS- and Ionic Liquid-Coated Quartz Crystal Microbalance Sensors for Detection and Molecular Weight Determination of Organic Vapors" (2014). LSU Doctoral Dissertations. 3323 (Year: 2014).*

(Continued)

Primary Examiner — Jill A Warden
Assistant Examiner — Quocan B Vo
(74) Attorney, Agent, or Firm — Law Office of Katsuhiro Arai

(57) ABSTRACT

A gas sensor offering high gas identification property includes: a first gas detection element having a first oscillator, as well as a first gas-adsorption film which is provided on the first oscillator and constituted by two or more fluorine resins including vinylidene fluoride resin; a second gas detection element having a second oscillator, as well as a second gas-adsorption film which is provided on the second oscillator and constituted by two or more fluorine resins including vinylidene fluoride resin and which has adsorption characteristics different from those of the first adsorption film; and a detection circuitry that detects the resonance frequencies of the first and second gas detection elements.

12 Claims, 5 Drawing Sheets

(52) U.S. Cl.
CPC .......... *G01N 2291/021* (2013.01); *G01N 2291/0256* (2013.01)

(58) Field of Classification Search
CPC .... G01N 5/02; G01N 29/036; G01N 33/0047; G01N 2291/0256; G01N 2291/021; G01N 2291/014
See application file for complete search history.

(56) References Cited

U.S. PATENT DOCUMENTS

| | | | | |
|---|---|---|---|---|
| 6,355,749 | B1* | 3/2002 | Chung | C08F 214/22 526/195 |
| 2004/0026246 | A1* | 2/2004 | Chapples | G01N 27/4074 204/424 |
| 2008/0085212 | A1* | 4/2008 | Adams | G01N 29/036 422/50 |
| 2011/0266919 | A1 | 11/2011 | Ikehara et al. | |
| 2013/0009517 | A1* | 1/2013 | Do | G01N 29/022 310/313 R |
| 2014/0364325 | A1* | 12/2014 | Cable | G01N 33/0031 506/7 |

FOREIGN PATENT DOCUMENTS

| | | |
|---|---|---|
| CN | 103411904 A | 11/2013 |
| JP | H09297096 A | 11/1997 |
| JP | 2006053059 A | 2/2006 |
| TW | 201201900 A | 1/2012 |
| WO | 2016003272 A1 | 1/2016 |

OTHER PUBLICATIONS

Plotner et al. "Miniaturized gas monitoring system employing several SAW sensors" 2001 IEEE International Frequency Control Symposium and PDA Exhibition (Year: 2001).*

"Phthalocyanine Blue BN" Chemicalland21, 2011, captured using web.archive.org (Year: 2011).*

Buckley et al. "Electrostrictive Properties of Poly(vinylidenefluoride-trifluoroethylene-chlorotrifluoroethylene)" Chemistry of Materials 2002 14 (6), 2590-2593 (Year: 2002).*

A Notification of Examination Opinions with Search Report issued by Taiwan Intellectual Property Office, dated Oct. 31, 2018, for Taiwan counterpart application No. 106121389.

A First Office Action issued by the State Intellectual Property Office of China dated Jun. 18, 2019 for Chinese counterpart application No. 201710674765.7 (9 pages).

* cited by examiner

GAS SENSOR

BACKGROUND

Field of the Invention

The present invention relates to a gas sensor capable of detecting gaseous species.

Description of the Related Art

Gas sensors include those that use a gas molecule detection element constituted by, for example, a crystal oscillator on which a gas molecule selection material having gas identification property is provided as an adsorption film, to measure a change in mass resulting from adsorption of gas molecules and thereby detect gas. For the adsorption film, a plasma-polymerized amino acid film in which an ionic liquid is permeated is used, for example, and a gas sensor that detects methanol, ethanol, and other alcohols using multiple gas molecule detection elements whose adsorption films contain ionic liquids of different concentrations, has been proposed (refer to Patent Literature 1). Also, use of PTFE and PE (polytetrafluoroethylene and polyethylene), and PCTFE (polychlorotrifluoroethylene), to discriminate acetone and methanol has been proposed (refer to Patent Literature 2).

BACKGROUND ART LITERATURES

[Patent Literature 1] Japanese Patent Laid-open No. 2006-53059
[Patent Literature 2] Japanese Patent Laid-open No. Hei 9-297096

SUMMARY

If a plasma polymerization film is used as the adsorption film, however, problems arise such as the film-forming process taking a long time and the film properties deteriorating over time. In addition, use of PTFE, PCTFE, or other fluorine organic film as the adsorption film presents problems in terms of gas identification property and sensitivity.

In light of the aforementioned situations, an object of the present invention is to provide a gas sensor offering high gas identification property.

Any discussion of problems and solutions involved in the related art has been included in this disclosure solely for the purposes of providing a context for the present invention, and should not be taken as an admission that any or all of the discussion were known at the time the invention was made.

To achieve the aforementioned object, the gas sensor pertaining to an embodiment of the present invention has a first gas detection element, a second gas detection element, and a detection part.

The first gas detection element has a first oscillator, as well as a first adsorption film which is provided on the first oscillator and formed using two or more types of fluorine resins including vinylidene fluoride resin.

The second gas detection element has a second oscillator, as well as a second adsorption film which is provided on the second oscillator and formed using two or more types of fluorine resins including vinylidene fluoride resin and which has adsorption characteristics different from those of the first adsorption film.

The detection part detects changes in the resonance frequencies of the first and second gas detection elements.

According to this constitution of the present invention, high gas identification property is achieved because an adsorption film having different adsorption characteristics is provided in each gas detection element.

A third gas detection element having a third oscillator, as well as a third adsorption film which is provided on the third oscillator and which contains a cyanine pigment, may be provided further.

According to this constitution, a gas different from the gases detected by the other gas detection element can be detected. For example, ammonia can be detected using the gas detection element on which the adsorption film containing a cyanine pigment is provided.

The first adsorption film is formed using the vinylidene fluoride resin and trifluoroethylene, while the second adsorption film is formed using the vinylidene fluoride resin, chlorotrifluoroethylene resin, and trifluoroethylene.

By using trifluoroethylene in the first adsorption film and also in the second adsorption film, as described above, forming the adsorption films becomes easy. To be specific, the vinylidene fluoride resin used in the first adsorption film and also in the second adsorption film has a very high degree of crystallinity, which means that the vinylidene fluoride resin has low solubility in solvents and will separate quickly even if it does dissolve, and it becomes difficult to manage the vinylidene fluoride resin. By copolymerizing the vinylidene fluoride resin with trifluoroethylene, however, its crystallization can be controlled and thus forming the films becomes easy.

A fourth gas detection element having a fourth oscillator, as well as a fourth adsorption film which is provided on the fourth oscillator and formed using vinylidene fluoride resin, chlorotrifluoroethylene resin, and trifluoroethylene at a blending ratio different from that used for the second adsorption film, and which has adsorption characteristics different from those of the first adsorption film or second adsorption film, may be provided further.

By providing the fourth gas detection element having the fourth adsorption film which is formed at a blending ratio different from that used for the second adsorption film and which has adsorption characteristics different from those of the first adsorption film or second adsorption film, as described above, the gas identification property improves further.

The first adsorption film is formed using the vinylidene fluoride resin, chlorotrifluoroethylene resin and trifluoroethylene, while the second adsorption film is formed using the vinylidene fluoride resin, chlorotrifluoroethylene resin, and trifluoroethylene at a blending ratio different from that used for the first adsorption film.

As described above, the gas detection elements can have adsorption films with different adsorption characteristics, which is achieved by using the same multiple fluorine resin materials at different blending ratios to form the adsorption films.

The gas sensor may further have a chamber and a processing part.

The chamber houses the gas detection elements.

The processing part calculates changes in the vibration resonance frequencies of the gas detection elements from the detected resonance frequencies, and then specifies the gas inside the chamber based on the calculated results.

As described above, according to the present invention a gas sensor offering high gas identification property by using multiple gas detection elements, each having a different adsorption film, can be obtained.

For purposes of summarizing aspects of the invention and the advantages achieved over the related art, certain objects and advantages of the invention are described in this disclosure. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

Further aspects, features and advantages of this invention will become apparent from the detailed description which follows.

BRIEF DESCRIPTION OF THE DRAWINGS

These and other features of this invention will now be described with reference to the drawings of preferred embodiments which are intended to illustrate and not to limit the invention. The drawings are greatly simplified for illustrative purposes and are not necessarily to scale.

DESCRIPTION OF THE SYMBOLS

Figure 1:
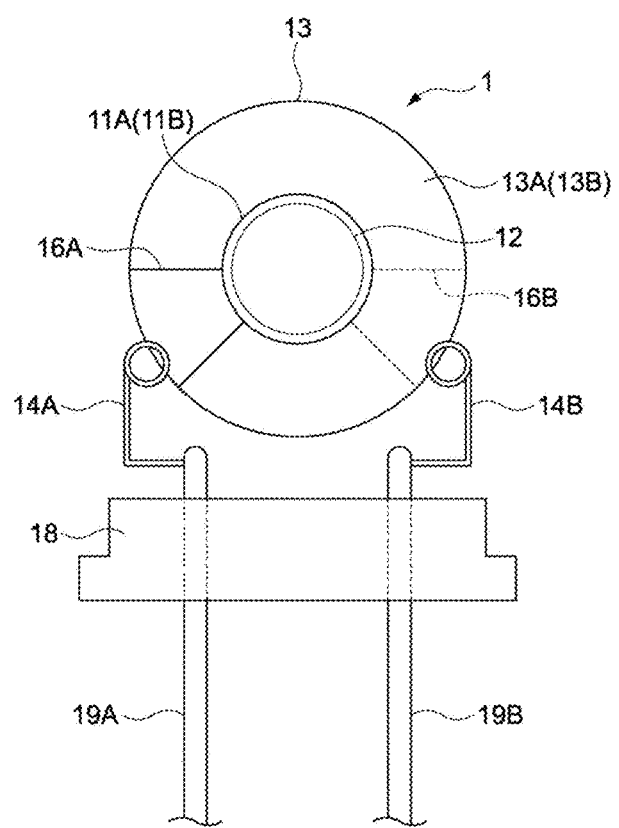
FIG. 1 is a front view of the gas detection element pertaining to an embodiment of the present invention.

1 Detection element
1b, 1c, 1d Gas detection element
2 Gas sensor
5 Detection circuitry
6 Processing part (Computing unit)
12b, 12c, 12d Adsorption film
13 Crystal oscillator

DETAILED DESCRIPTION OF EMBODIMENTS

An embodiment of the present invention is explained below by referring to the drawings.

The gas sensor pertaining to the present invention has multiple gas detection elements. The gas detection elements are each constituted in such a way that an adsorption film that adsorbs a specific gas is provided on a crystal oscillator that serves as a vibrator. Since the resonance frequency of a given crystal oscillator decreases in proportion to the weight of the gas that has been adsorbed onto its adsorption film, the gaseous species can be detected based on the measured result of the amount of change in the resonance frequency of each crystal oscillator.

While crystal oscillators with a resonance frequency of 9 MHz are used for the gas detection elements in this embodiment, the present invention is not limited to this application. For example, ceramic oscillators, surface acoustic wave elements, cantilevers, diaphragms, etc., can also be used, besides crystal oscillators, so long as they are able to detect an increase in weight, increase in expansive stress, or other physical change resulting from adsorption of gas on the adsorption film, and to convert the detected physical change into an electrical signal.

[Constitution of Gas Detection Element]

FIG. 1 is a front view of a detection element 1 (1a to 1d in FIG. 2) constituting a part of the gas sensor pertaining to this embodiment.

The detection element 1 has a crystal oscillator 13, electrodes 11A (11B), an adsorption film 12, lead lands 16A, 16B, leads 14A, 14B, pin terminals 19A, 19B, and a holder 18.

The crystal oscillator 13 is an AT-cut crystal plate. On opposing principal faces 13A, 13B of the crystal oscillator 13, the electrodes 11A, 11B have been formed, respectively, each through patterning of a thin metal film into a specified shape.

The adsorption film 12 is formed on the electrode 11A.

The lead land 16A is integrally formed with the electrode 11A, while the lead land 16B is integrally formed with the electrode 11B.

The leads 14A, 14B are each made of a metallic spring material, and are placed in parallel with each other.

One end of the lead 14A is electrically connected to the electrode 11A via the lead land 16A, while the other end is connected to the pin terminal 19A. One end of the lead 14B is electrically connected to the electrode 11B via the lead land 16B, while the other end is connected to the pin terminal 19B.

The holder 18 is made of an insulating member, and has through holes that let the pin terminals 19A, 19B pass through, respectively. As the crystal oscillator 13 is held in such a way that the pin terminals 19A, 19B pass through the through holes in the holder 18, the crystal oscillator 13 is vibratably supported by the holder 18.

The pin terminals 19A, 19B of the detection element 1 are connected to an oscillation circuitry which will be described later, so that a drive voltage is applied to the detection element 1. When the drive voltage is applied to the detection element 1, the crystal oscillator 13 vibrates at its natural resonance frequency (9 MHz in this example).

Then, as the adsorption film 12 adsorbs gas, its mass changes and the oscillation frequency of the crystal oscillator 13 drops according to the adsorbed amount of gas.

[Constitution of Gas Sensor]

Figure 2:
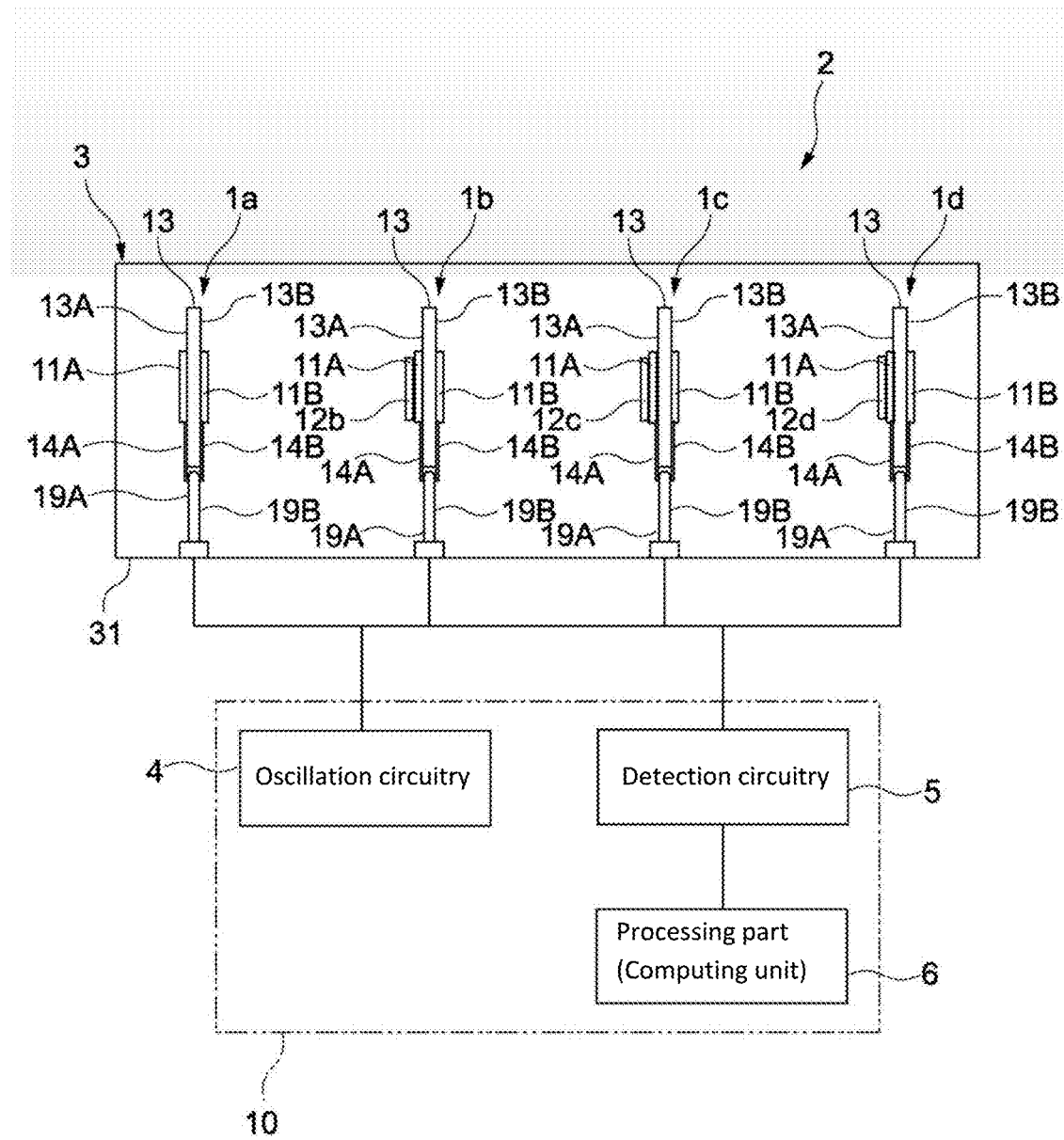
FIG. 2 is a schematic drawing illustrating the constitution of the gas sensor pertaining to an embodiment of the present invention.

FIG. 2 is a drawing illustrating the constitution of a gas sensor having multiple detection elements 1 shown in FIG. 1.

As shown in FIG. 2, the gas sensor 2 has a gas sensor unit 3, and a controller 10. The controller 10 has an oscillation circuitry 4, a detection circuitry 5, and a processing part (computing unit) 6.

The gas sensor unit 3 has a chamber 31, one detection element 1a, and three gas detection elements 1b to 1d.

The chamber 31 houses the detection element 1a and gas detection elements 1b to 1d that are arranged with a specific spacing in between. The chamber 31 is such that the gas to be detected can be introduced into it.

The detection element 1a and three gas detection elements 1b to 1d have a basic structure similar to that of the detection element 1 shown in FIG. 1, while the detection elements 1a to 1d are each different in terms of whether or not the adsorption film 12 is provided on the electrode 11A and the type of the adsorption film 12, if provided. The adsorption films 12b to 12d provided on the gas detection elements 1b to 1d, respectively, have adsorption characteristics that are different from the others.

The adsorption film 12 is not formed on the detection element 1a, and therefore the detection element 1a is used as a reference.

The gas detection element 1b which serves as a first gas detection element has a first oscillator 13, as well as an adsorption film 12b which is provided on the first oscillator 13 and serves as a first adsorption film.

The adsorption film 12b is constituted by a copolymer which in turn is formed using vinylidene fluoride resin (polyvinylidene fluoride; hereinafter referred to as "PVDF") and trifluoroethylene (hereinafter referred to as "TrFE"). To be specific, PVDF and TrFE were blended at a blending ratio by weight of 8:2 and copolymerized accordingly, after which the resulting powder was dissolved in methyl ketone to produce a solution and this solution was applied onto the electrode 11A to a specific thickness, or thickness of 1 μm here, using a spin-coater, and then the solvent was volatilized in a drying oven, to form the adsorption film 12b.

The gas detection element 1c which serves as a second gas detection element has a second oscillator 13, as well as an adsorption film 12c which is provided on the second oscillator 13 and serves as a second adsorption film.

The adsorption film 12c is constituted by a copolymer which in turn is formed using PVDF, TrFE, and chlorotrifluoroethylene resin (polychlorotrifluoroethylene; hereinafter referred to as "PCTFE"). To be specific, PVDF, TrFE, and PCTFE were blended at a blending ratio by weight of 65:25:10 and copolymerized accordingly, after which the resulting powder was dissolved in methyl ketone to produce a solution and this solution was applied onto the electrode 11A to a specific thickness, or thickness of 1 μm here, using a spin-coater, and then the solvent was volatilized in a drying oven, to form the adsorption film 12c.

The gas detection element 1d which serves as a third gas detection element has a third oscillator 13, as well as an adsorption film 12d which is provided on the third oscillator 13 and serves as a third adsorption film.

The adsorption film 12d is formed using a cyanine pigment. For the cyanine pigment, 1,1'-dibutyl 3,3,3',3'-tetramethyl-4,5,4',5' dibenzoindodicarbo cyanine bromide (Product Number NK3567 manufactured by Nippon Kankoh-Shikiso Kenkyusho Co., Ltd.) was used. This NK3567 was dissolved in tetrafluoropropanol (TFP) to produce a solution and this solution was applied onto the electrode 11A to a specific thickness, or thickness of 0.1 μm here, using a spin-coater, and then the solvent was volatilized in a drying oven, to form the adsorption film 12d.

Here, it should be noted that, while the film thickness of the adsorption film 12b and that of the adsorption film 12c were both 1 μm, the film thickness of the adsorption film 12d was set to 0.1 μm, so that the resonance frequencies of the three types of adsorption films 12b, 12c, 12d would change, due to adsorption of acetone, by amounts in the same order of magnitude per unit surface area.

Also, the adsorption films 12b to 12d of the gas detection elements 1b to 1d each have the same film formation area, which is approx. 0.2 cm², for example.

The chemical formula of the PVDF mentioned above is as follows.

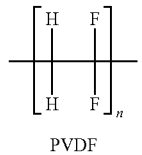

[Chemical Formula 1]

PVDF

The PVDF has a straight-chain structure constituted by $CF_2$ and $CH_2$ alternately bonded to each other, and exhibits high dielectric characteristics because the fluorine atoms can turn freely.

The chemical formula of the TrFE mentioned above is as follows.

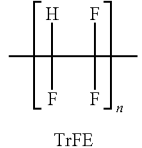

[Chemical Formula 2]

TrFE

The chemical formula of the PCTFE mentioned above is as follows.

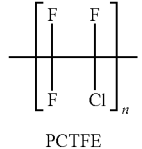

[Chemical Formula 3]

PCTFE

The adsorption films 12b, 12d mentioned above are both formed using TrFE which is a fluorine resin.

This use of TrFE makes it easy to form the adsorption films. To be specific, the PVDF used in the adsorption film 12b and also in the adsorption film 12c has a very high degree of crystallinity, which means that the PVDF has low solubility in solvents and will separate quickly even if it does dissolve, and it becomes difficult to manage the PVDF. By copolymerizing the PVDF with TrFE, however, its crystallization can be controlled and thus forming the films becomes easy.

The oscillation circuitry 4 vibrates the respective crystal oscillators 13 of the detection element 1a and gas detection elements 1b to 1d at a specified frequency (9 MHz in this example).

The detection circuitry 5 detects the resonance frequencies of the detection element 1a and gas detection elements 1b to 1d. When gas or other detection target adsorbs onto the adsorption films 12b to 12d while the gas detection elements 1b to 1d are vibrating at a specified frequency due to the oscillation circuitry 4, the resonance frequencies of the crystal oscillators 13 of the respective gas detection elements 1b to 1d change. The detection circuitry 5 outputs electrical signals corresponding to the detected resonance frequencies, to the processing part 6.

The processing part 6 calculates the changes in the vibration resonance frequencies of the respective gas detection elements 1b to 1d based on the electrical signals of the detection element 1a and respective gas detection elements 1b to 1d that have been input from the detection circuitry 5 and, from the calculated results of the changes in vibration resonance frequencies, it specifies the type of the gas that was introduced into the chamber 31.

The changes in vibration resonance frequencies that have been calculated, and the type of gas that has been specified, by the processing part 6, can be output to and displayed on a display device, etc., which is not illustrated, for example, so that the measurer can check the measured results.

[Characteristics of Adsorption Films and Detection of Gas Utilizing these Characteristics]

Next, the characteristics of the adsorption films 12b to 12d that are formed on the respective gas detection elements 1b to 1d mentioned above, are explained.

Table 1 is a table showing the adsorption characteristics, with respect to various types of gases, of the adsorption film 12b and the adsorption film 12c that have each been formed to a surface area of 0.2 cm$^2$ and film thickness of 1 μm. These characteristics were evaluated using a QCM measuring instrument (Model Number: THQ-100P) manufactured by Tamadevice Co., Ltd. For the gases, volatile gases such as acetone, toluene, ethanol, ammonia, and formaldehyde, were used. The gas detection elements were placed in the QCM measuring instrument, after which the gases were introduced, one by one, into the QCM measuring instrument and caused to contact the gas detection elements at a specified flow rate, or flow rate of 300 sccm here, and the adsorption characteristics of the adsorption film 12b and those of the adsorption film 12c were evaluated by plotting the maximum changes occurring in their resonance frequencies.

TABLE 1

| Change in frequency (Hz) | Adsorption film 12b | Adsorption film 12c |
| --- | --- | --- |
| Acetone | 3250 | 2800 |
| Toluene | 105 | 850 |
| Ethanol | 89 | 104 |
| Ammonia | 32 | 35 |
| Formaldehyde | 40 | 41 |

As shown in Table 1, the adsorption film 12b and the adsorption film 12c both have characteristics of adsorbing acetone, although the adsorption amounts are slightly different. When adsorption of toluene is concerned, however, the adsorption film 12c containing PCTFE adsorbs a far greater amount than the adsorption film 12b not containing PCTFE.

Figure 4:
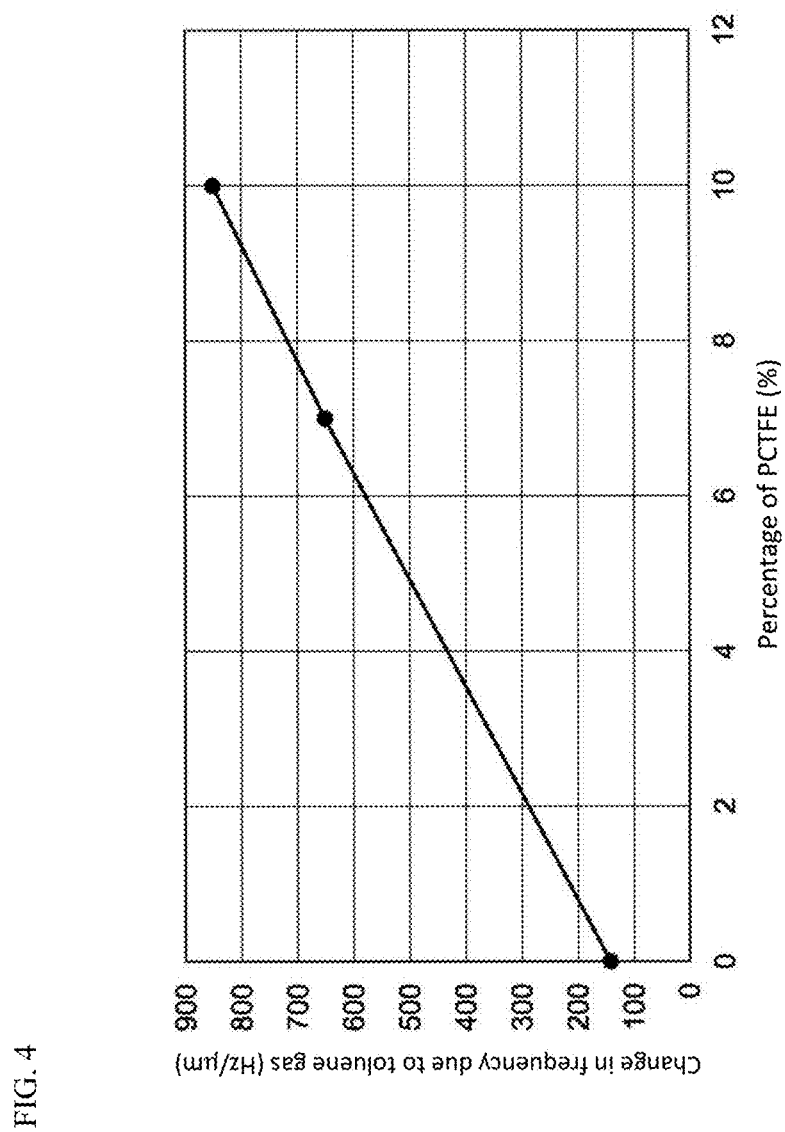
FIG. 4 is a graph showing the relationship between the blending percentage of PCTFE in an adsorption film, and the change in its resonance frequency when toluene gas is adsorbed.

FIG. 4 shows the characteristics of an adsorption film that has been formed to a film thickness of 1 μm using PCTFE and PVDF, and represents the relationship between the blending percentage of PCTFE, and the change in the resonance frequency of the crystal oscillator 13 due to adsorption of toluene gas.

As shown in FIG. 4, the higher the blending percentage of PCTFE, the greater the change in resonance frequency due to adsorption of toluene gas becomes, where the amount of PCTFE is roughly proportional to the amount of change in resonance frequency.

Figure 3:
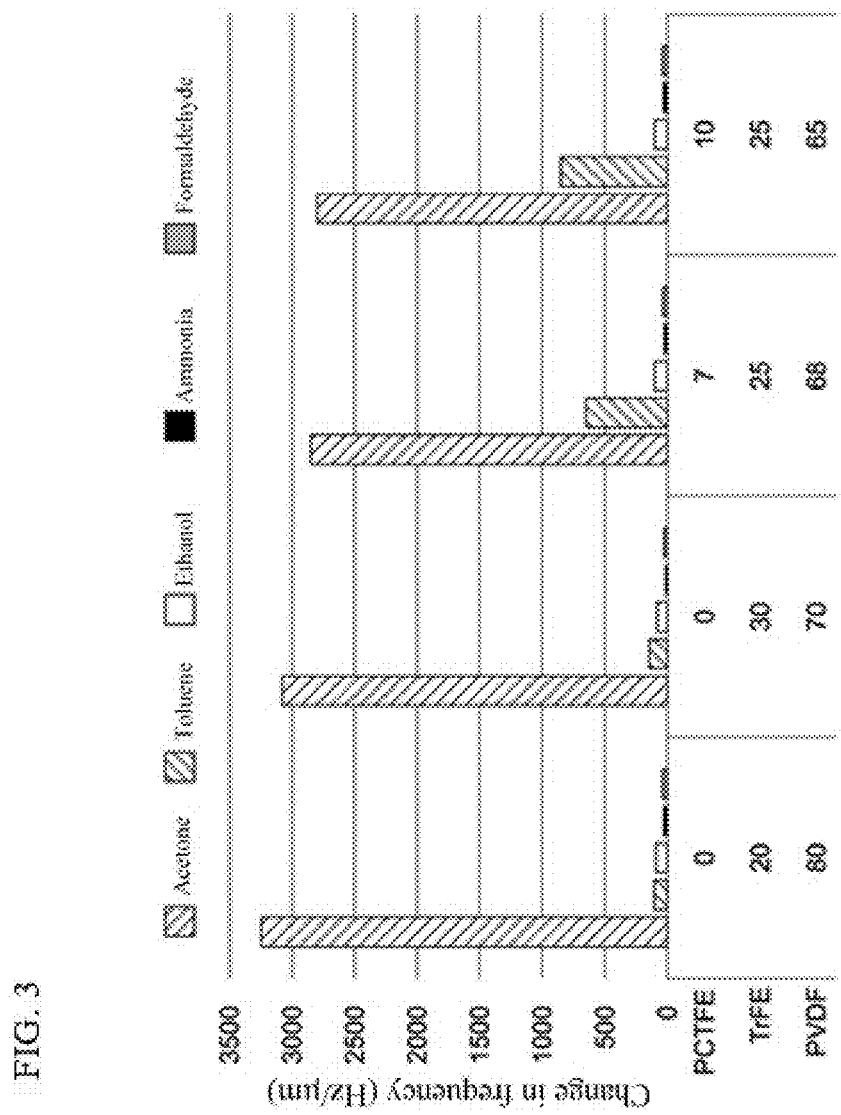
FIG. 3 is a graph comparing how the resonance frequencies of the multiple gas detection elements, whose adsorption films are formed using PVDF and PCTFE at different blending ratios, change when various types of gases are adsorbed.

FIG. 3 shows the adsorption characteristics, with respect to various types of gases, of adsorption films that have each been formed to a film thickness of 1 μm using PCTFE, TrFE, and PVDF at different composition ratios by weight. For the gases, acetone, toluene, ethanol, ammonia, and formaldehyde were used.

In FIG. 3, the results shown represent the films using PCTFE, TrFE, and PVDF at blending ratios by weight of 0:20:80, 0:30:70, 7:25:68, and 10:25:65, respectively, from the left.

As shown in FIG. 3, all films have characteristics of adsorbing acetone; however, the films that were formed using PCTFE (two films on the right in the graph) adsorb more toluene compared to the films that were formed without using PCTFE (two films on the left in the graph).

Figure 5:
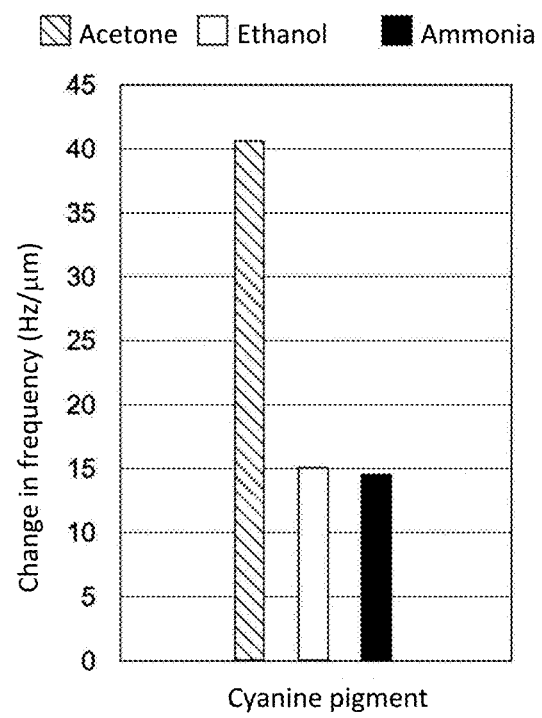
FIG. 5 is a graph showing an example of how the frequency of an adsorption film using cyanine pigment changes with types of gases.

FIG. 5 shows the characteristics of the film used as the adsorption film 12d of the gas detection element 1d, or specifically a film formed to a film thickness of 1 nm using a cyanine pigment. For the cyanine pigment, Product Number "NK3567" manufactured by Nippon Kankoh-Shikiso Kenkyusho Co., Ltd., was used.

As shown in FIG. 5, the adsorption film 12d has characteristics of adsorbing acetone, ethanol, and ammonia. Additionally, while not shown in FIG. 5, the adsorption film 12d also has characteristics of adsorbing toluene.

As shown in FIG. 5, the adsorption film 12d exhibits a change of approx. 40.5 Hz in its resonance frequency per 1 nm when it adsorbs acetone. Since the adsorption film 12d is formed to a film thickness of 0.1 μm, this change in resonance frequency corresponds to an equivalent change in resonance frequency of approx. 4050 Hz per 0.1 μm of film thickness.

Similarly, the film exhibits a change in its resonance frequency of approx. 15 Hz when it adsorbs ethanol, and of 14.5 Hz when it adsorbs ammonia, per 1 nm, and these changes in resonance frequency correspond to equivalent changes in resonance frequency of approx. 1500 Hz and 1450 Hz, per 0.1 μm of film thickness, respectively.

On the other hand, the film exhibits a change in its resonance frequency of approx. 10.6 Hz per 1 nm when it adsorbs toluene. Since the adsorption film 12d is formed to a film thickness of 0.1 μm, this change in resonance frequency corresponds to an equivalent change in resonance frequency of approx. 1060 Hz per 0.1 μm of film thickness.

As described above, in this embodiment the film thicknesses of the adsorption films 12b to 12d provided on the respective gas detection elements 1b to 1d are adjusted in consideration of the adsorption characteristics of each of the adsorption films. Here, the adjustments are made so that, when acetone is adsorbed, the resonance frequencies of all gas detection elements 1b to 1d change by values in the same four-digit orders of magnitude.

By utilizing the adsorption characteristics of the respective adsorption films 12b to 12d as described above, the aforementioned gas sensor 2 can detect acetone, toluene, ethanol, or ammonia, for example.

To be specific, if a change in resonance frequency of 1000 Hz or more is detected in all of the gas detection elements 1b, 1c, 1d, then it can be determined that the detection target gas is acetone.

On the other hand, if a change in resonance frequency of 500 Hz or less is detected in the gas detection element 1b and at the same time a change in resonance frequency of 500 Hz or more is detected in both the gas detection elements 1c and 1d, then it can be determined that the detection target gas is toluene.

Or, if the change in resonance frequency is around 100 Hz or less in both the gas detection elements 1b and 1c and at the same time the gas detection element 1d exhibits a change in resonance frequency of 1000 Hz or more, then it can be determined that the detection target gas is ethanol or ammonia.

It should be noted that, in this embodiment, an example is presented where the film formation area of the adsorption film of each sensor is 0.2 cm$^2$, the film thickness of the adsorption film 12$b$ of the gas detection element 1$b$ and that of the adsorption film 12$c$ of the gas detection element 1$c$ are both 1 μm, and the film thickness of the adsorption film 12$d$ of the gas detection element 1$d$ is 0.1 μm, and based on the gas adsorption characteristics of the respective adsorption films 12$b$ to 12$d$ as determined by these film formation area and film thicknesses, the values of how much the resonance frequency would change, which are used as the bases for specifying the types of detection target gases, as described above, are determined.

In this embodiment, both the adsorption films 12$b$ and 12$c$ are formed using two or more types of fluorine resins including PVDF. While the adsorption film 12$b$ is formed using PVDF and TrFE, and the adsorption film 12$c$ is formed using PVDF, TrFE, and PCTFE, the fluorine resin materials are not limited to the foregoing.

For the fluorine resins, the following may be used.

For example, any resins selected from tetrafluoroethylene resins (polytetrafluoroethylenes, hereinafter referred to as "PTFE"), tetrafluoroethylene perfluoroalkyl vinyl ether copolymer resins (perfluoroalkoxy alkanes hereinafter referred to as "PFA"), tetrafluoroethylene-hexafluoropropylene copolymer resins (perfluoroethylene propene copolymers, hereinafter referred to as "FEP"), tetrafluoroethylene-ethylene copolymer resins (ethylene-tetrafluoroethylene copolymers, hereinafter referred to as "EFTE"), chlorotrifluoroethylene-ethylene copolymer resins (ethylene-chlorotrifluoroethylene copolymers, hereinafter referred to as "ECTFE"), tetrafluoroethylene-perfluorodioxole copolymer resins (tetrafluoroethylene-perfluorodioxole copolymers, hereinafter referred to as "TE/PDD") and vinyl fluoride resins (polyvinyl fluorides, hereinafter referred to as "PVF"), may be used.

In addition, while the aforementioned embodiment used two gas detection elements, each having an adsorption film which is formed using two or more types of fluorine resins including PVDF, there may be three or more such gas detection elements. For example, a fourth gas detection element having a fourth crystal oscillator, as well as a fourth adsorption film provided on the fourth crystal oscillator, may be provided further in addition to the gas detection elements 1$b$ and 1$c$ explained in the aforementioned embodiment.

This fourth adsorption film is formed using PVDF, TrFE, and PCTFE, just like the adsorption film 12$c$ is, but their blending ratio is different from that used for the adsorption film 12$c$, and therefore this adsorption film has adsorption characteristics different from those of the adsorption film 12$b$ or those of the adsorption film 12$c$. Because of this, the adsorbed amount of toluene can be detected by utilizing, for example, the characteristics that the content of PCTFE has a virtually linear relationship with the change in resonance frequency due to adsorption of toluene.

In addition, the aforementioned embodiment is such that the two gas detection elements 1$b$, 1$c$ are each a gas detection element having an adsorption film which is formed using two or more types of fluorine resins including PVDF, and that these gas detection elements are used to identify acetone and toluene; however, the present invention is not limited to this application.

For example, a first gas detection element having a first adsorption film which is formed using PVDF, TrFE, and PCTFE, and a second gas detection element having a second adsorption film which is formed using PVDF, TrFE, and PCTFE at a blending ratio different from that used for the first adsorption film, may be provided instead of the gas detection elements 1$b$, 1$c$, and these first gas detection element and second gas detection element may be used to identify acetone and toluene. To be specific, by setting the blending percentage of PCTFE in the second adsorption film higher than the blending percentage of PCTFE in the first adsorption film, the second gas detection element having the second adsorption film whose PCTFE blending percentage is higher, can be used to detect toluene by utilizing the characteristics that the content of PCTFE is roughly proportional to the change in resonance frequency due to adsorption of toluene.

(Gas Detection Method)

Next, the gas detection method using the aforementioned gas sensor 2 is explained using FIG. 2.

As described above, the gas sensor unit 3 of the gas sensor 2 has one detection element 1$a$ used for reference, and three gas detection elements 1$b$ to 1$d$, provided in it. After the detection target gas has been introduced into the chamber 31, the oscillation circuitry 4 is actuated and the crystal oscillators 13 of the detection element 1$a$ and respective gas detection elements 1$b$ to 1$d$ are vibrated at a specified frequency (9 MHz in this example).

Next, the resonance frequencies of the detection element 1$a$ and respective gas detection elements 1$b$ to 1$d$ are detected using the detection circuitry 5. Electrical signals corresponding to the detected resonance frequencies are input to the processing part 6.

Using the resonance frequency of the detection element 1$a$ as reference, the processing part 6 calculates the changes in the resonance frequencies of the respective gas detection elements 1$b$ to 1$d$, from the resonance frequency of the detection element 1$a$ and also from the resonance frequency of each of the gas detection elements 1$b$ to 1$d$. Then, the detection target gaseous species is specified based on the calculated results.

The type of the detection target gas is specified as follows.

The processing part 6 determines, when a change in resonance frequency of 1000 Hz or more is detected in all of the gas detection elements 1$b$, 1$c$, and 1$d$, that the detection target gas is acetone.

On the other hand, the processing part 6 determines, when a change in resonance frequency of 500 Hz or less is detected in the gas detection element 1$b$ and at the same time a change in resonance frequency of 500 Hz or more is detected in both the gas detection elements 1$c$ and 1$d$, that the detection target gas is toluene.

Or, the processing part 6 determines, when the change in resonance frequency is around 100 Hz or less in both the gas detection elements 1$b$ and 1$c$ and at the same time the gas detection element 1$d$ exhibits a change in resonance frequency of 1000 Hz or more, that the detection target gas is ethanol or ammonia.

As described above, a gas sensor offering improved gas identification property can be obtained by providing multiple gas detection elements, each having a different adsorption film.

In addition, a gas sensor offering improved gas identification property can be obtained by providing adsorption films whose adsorption characteristics are different, where each adsorption film is formed using two or more types of fluorine resins including PVDF.

The foregoing explained an embodiment of the present invention; however, the present invention is not limited to the aforementioned embodiment and it goes without saying that various changes can be added to the present invention.

In the present disclosure where conditions and/or structures are not specified, a skilled artisan in the art can readily provide such conditions and/or structures, in view of the present disclosure, as a matter of routine experimentation. Also, in the present disclosure including the examples described above, any ranges applied in some embodiments may include or exclude the lower and/or upper endpoints, and any values of variables indicated may refer to precise values or approximate values and include equivalents, and may refer to average, median, representative, majority, etc. in some embodiments. Further, in this disclosure, "a" may refer to a species or a genus including multiple species, and "the invention" or "the present invention" may refer to at least one of the embodiments or aspects explicitly, necessarily, or inherently disclosed herein. The terms "constituted by" and "having" refer independently to "typically or broadly comprising", "comprising", "consisting essentially of", or "consisting of" in some embodiments. In this disclosure, any defined meanings do not necessarily exclude ordinary and customary meanings in some embodiments.

The present application claims priority to Japanese Patent Application No. 2016-156089, filed Aug. 9, 2016, the disclosure of which is incorporated herein by reference in its entirety including any and all particular combinations of the features disclosed therein.

It will be understood by those of skill in the art that numerous and various modifications can be made without departing from the spirit of the present invention. Therefore, it should be clearly understood that the forms of the present invention are illustrative only and are not intended to limit the scope of the present invention.

I claim:

1. A gas sensor, comprising:
a first gas-detection element having a first oscillator, as well as a first gas-adsorption film which is provided on the first oscillator and made of a copolymer constituted by two or more fluorine resins including vinylidene fluoride resin and trifluoroethylene, wherein a resonance frequency of the first oscillator is changed when the first gas-adsorption film adsorbs gas;
a second gas-detection element having a second oscillator, as well as a second gas-adsorption film which is provided on the second oscillator and made of a copolymer constituted by two or more fluorine resins including vinylidene fluoride resin and trifluoroethylene, wherein a blending ratio of the two or more fluorine resins used for the second gas-detection film is different from that used for the first gas-detection film in a manner that the second gas-adsorption film has gas-adsorption characteristics different from those of the first gas-adsorption film wherein a resonance frequency of the second oscillator is changed when the second gas-adsorption film adsorbs gas; and
a detection circuitry that detects resonance frequencies of the first and second gas-detection elements.

2. A gas sensor according to claim 1, further comprising:
a third gas-detection element having a third oscillator, as well as a third adsorption film which is provided on the third oscillator and which contains a cyanine pigment wherein a resonance frequency of the third oscillator is changed when the third gas-adsorption film adsorbs gas.

3. A gas sensor according to claim 1, wherein:
the first gas-adsorption film is made of a copolymer constituted by the vinylidene fluoride resin and trifluoroethylene; and
the second gas-adsorption film is made of a copolymer constituted by the vinylidene fluoride resin, chlorotrifluoroethylene resin, and trifluoroethylene.

4. A gas sensor according to claim 2, wherein:
the first gas-adsorption film is made of a copolymer constituted by the vinylidene fluoride resin and trifluoroethylene; and
the second gas-adsorption film is made of a copolymer constituted by the vinylidene fluoride resin, chlorotrifluoroethylene resin, and trifluoroethylene.

5. A gas sensor according to claim 3, further comprising:
a fourth gas-detection element having a fourth oscillator, as well as a fourth gas-adsorption film which is provided on the fourth oscillator and made of a copolymer constituted by vinylidene fluoride resin, chlorotrifluoroethylene resin, and trifluoroethylene at a blending ratio different from that used for the second gas-adsorption film, and which has gas-adsorption characteristics different from those of the first gas-adsorption film and those of the second gas-adsorption film wherein a resonance frequency of the fourth oscillator is changed when the fourth gas-adsorption film adsorbs gas.

6. A gas sensor according to claim 4, further comprising:
a fourth gas-detection element having a fourth oscillator, as well as a fourth gas-adsorption film which is provided on the fourth oscillator and made of a copolymer constituted by vinylidene fluoride resin, chlorotrifluoroethylene resin, and trifluoroethylene at a blending ratio different from that used for the second gas-adsorption film, and which has gas-adsorption characteristics different from those of the first gas-adsorption film and those of the second gas-adsorption film wherein a resonance frequency of the fourth oscillator is changed when the fourth gas-adsorption film adsorbs gas.

7. A gas sensor according to claim 1, wherein:
the first gas-adsorption film is made of a copolymer constituted by the vinylidene fluoride resin, chlorotrifluoroethylene resin, and trifluoroethylene; and
the second gas-adsorption film is made of a copolymer constituted by the vinylidene fluoride resin, chlorotrifluoroethylene resin, and trifluoroethylene at a blending ratio different from that used for the first gas-adsorption film.

8. A gas sensor according to claim 2, wherein:
the first gas-adsorption film is made of a copolymer constituted by the vinylidene fluoride resin, chlorotrifluoroethylene resin, and trifluoroethylene; and
the second gas-adsorption film is made of a copolymer constituted by the vinylidene fluoride resin, chlorotrifluoroethylene resin, and trifluoroethylene at a blending ratio different from that used for the first gas-adsorption film.

9. A gas sensor according to claim 1, further comprising:
a chamber that houses the respective gas detection elements; and
a computing unit that calculates changes in resonance frequencies of the respective gas detection elements from the detected resonance frequencies, and then specifies a gas inside the chamber based on calculated results.

10. A gas sensor according to claim 1, wherein a thickness of the first gas-adsorption film and a thickness of the second gas-adsorption film are set differently wherein the resonance frequencies of the films are changed, to values of a same order of magnitude per unit surface area of each film when the films adsorb acetone.

11. A gas sensor according to claim 1, wherein a film formation area of the first gas-adsorption film and a film formation area of the second gas-adsorption film are substantially the same.

12. A gas sensor according to claim 1, further comprising a reference gas detection element on which no gas-adsorption film is provided.

* * * * *